United States Patent [19]

Leighton et al.

[11] 4,276,383
[45] Jun. 30, 1981

[54] CLOT LYSING TIMER

[75] Inventors: Stephen B. Leighton, Maplewood, N.J.; Genesio Murano, Bethesda, Md.; Allen Markowitz; Burt Chikadel, both of Gaithersburg, Md.

[73] Assignee: The United States of America as represented by the Department of Health, Education & Welfare, Washington, D.C.

[21] Appl. No.: 63,261

[22] Filed: Aug. 2, 1979

[51] Int. Cl.$^3$ .............................................. C12M 1/34
[52] U.S. Cl. .................................... 435/291; 435/808; 73/57; 73/64.1; 422/73
[58] Field of Search ............... 435/287, 288, 291, 296, 435/808, 809; 73/57, 64.1; 422/73; 356/39, 244

[56] References Cited

U.S. PATENT DOCUMENTS

| | | | |
|---|---|---|---|
| 2,776,021 | 1/1957 | Van Ackeren | 183/3 |
| 3,375,705 | 4/1968 | Kim | 73/57 |
| 3,411,343 | 11/1968 | Baird | 73/57 |
| 3,443,419 | 5/1969 | Gruitroy | 73/57 |
| 3,560,162 | 2/1971 | Mittleman | 23/253 |
| 3,605,010 | 9/1971 | Folus | 23/230 B |
| 3,605,010 | 9/1971 | Folus | 435/13 |
| 3,668,677 | 6/1972 | Higgs | 73/57 |
| 3,695,842 | 10/1972 | Mintz | 23/230 R |
| 3,772,910 | 11/1973 | McGinn | 73/57 |
| 3,781,118 | 12/1973 | Graham | 356/201 |
| 3,819,276 | 6/1974 | Kiess et al. | 73/64.1 |
| 3,847,482 | 11/1974 | Sokol | 356/244 |
| 3,853,710 | 12/1974 | Innerfield | 23/230 B |
| 3,948,730 | 4/1976 | Gagnon | 435/808 |
| 3,967,934 | 7/1976 | Seitz | 73/57 |
| 3,983,004 | 9/1976 | Trobisch | 23/230 B |
| 3,985,618 | 10/1976 | Innerfield | 23/230 B |
| 4,055,395 | 10/1977 | Honkawa | 356/244 |

FOREIGN PATENT DOCUMENTS 1197087  7/1970  United Kingdom ........................ 73/57

OTHER PUBLICATIONS

1979 FASEB Abstract Form, The Lysometer: An Automated Device for the Detection of Fibrin Dissolution, In Vitro, Jan. 2, 1979.
Wilkins, "New Instrument for Automatic Recording of Clot Lysis", American Journal Clinical Pathology, vol. 66, pp. 124-131, 1976.
Kieldgaard, "Urokinase-An Activator of Plasminogen from Human Urine", Biochimica et Biophysica Acta, vol. 24, pp. 283-289, (1957).
Folus, "A New Electromechanical Device for Measurement of Clot Lysis Times", Am. J. Clin. Path. 54, pp. 361-368, 1970.
Plough, "Urokinase, An Activator of Plasminogen from Human Urine, I. Isolation and Properties", Biochem. Biophys. S. Acta, 24, pp. 278-289, 1957.
Fletcher, "The Measurement of the Components of the Plasminogen-Plasm in System in Biological Fluids", Biochem. J. 56; pp. 677-682, 1954.
"Falling Ball Viscometry, Anal. Chem., Apr. 1965, vol. 37, No. 4, pp. 613-615.
Folus et al., "A New Electromechanical Device for Measurement of Clot Lysis Times, Am. J. Clin. Path. 54; pp. 361-368, 1970.
Fletcher, "The Measurement of the Components of the Plasminogen-Plasmin System in Biological Fluids, Biochem. J. 56, pp. 677-684, 1954.
Plough, "Urokinase, An Activator of Plasminogen from Human Urine, Biochem. Biophys. Acta 24, pp. 278-289, 1957.

*Primary Examiner*—Ernest G. Therkorn
*Attorney, Agent, or Firm*—Browdy and Neimark

[57] ABSTRACT

A clot lysing timing device consisting of a thermostatically controlled assembly including heated blocks formed with wells to receive precooled test tubes containing liquid with clots formed by the addition of thrombin to plasma (or to a mixture of fibrinogen and plasminogen) containing varying quantities of urokinase, streptokinase or plasmin. The blocks are maintained at 37° C. when a precooled test tube with such contents is placed in one of the 37° C. wells it activates a microswitch which starts a corresponding timer channel. An opaque sphere is placed on top of the clot. As the clot dissolves (at a rate depending on the quantity of lytic agent incorporated in the clot) the sphere travels to the bottom of the test tube, interrupting an infra red light beam, which stops the corresponding timer channel. The time counts from the respective timer channels can be selectively displayed on an LED digital readout device.

14 Claims, 5 Drawing Figures

CLOT LYSING TIMER

FIELD OF THE INVENTION

This invention relates to lysis detection apparatus, and more particularly to a system which can be employed to measure and display the time taken for a clot to be lysed by an enzyme incorporated in the clot.

BACKGROUND OF THE INVENTION

With the growing interest in the treatment of thromboembolism with lytic agents such as urokinase and sureptokinase, there has arisen a need for substantially automated means for measuring the lysis time of a preformed plasma (or fibrinogen) clot with more precision then has been heretofore available. Typical of previously available apparatus for this general purpose is the device disclosed in U.S. Pat. No. 3,605,010 to S. G. Folus, and also that disclosed in the publication of S. G. Folus and D. N. Kramer, entitled "A New Electromechanical Device for Measurement of Clot Lysis Times", Am. J. Clin. Path. 54: 361-368, 1970. Due to the relative complexity of the apparatus disclosed in these publications, it is not easy to obtain satisfactory operation thereof, and the apparatus includes numerous sources of error. It is preferable to perform the lysing time measurement in a simpler and more reliable manner. Various other procedures and devices have been developed in the past, relating to such time measurement, for example, as described in A. P. Fletcher, "The Measurement of the Components of the Plasminogen-Plasmin System in Biological Fluids", Biochem. J. 56; 677-682, 1954, and J. Plough et al, "Urokinase, An Activator of Plasminogen from Human Urine. I. Isolation and Properties", Biochem. Biophys. Acta, 24; 278-289, 1957. These further-described procedures and devices likewise fall short of filling the above-defined need.

A preliminary search of the patented prior art reveals the following prior U.S. patents of interest: Nos
- Seitz et al, 3,967,934
- Kim, 3,375,705
- Graham, 3,781,118
- Baird, Jr., 3,411,343
- Van Ackeren, 2,776,021
- Folus, 3,605,010
- Mintz, 3,695,842
- Mittleman, 3,560,162
- Trobisch et al, 3,983,004
- Innerfield, 3,985,618
- Innerfield, 3,853,710

SUMMARY OF THE INVENTION

The present invention employs the principle of measuring the time required for a small sphere to drop from a dissolving clot to the bottom of a test tube at a temperature of 37° C. Since the time required for clot dissolution is related to the concentration of the enzyme plasmin (produced by various activators), by a careful choice of suitable concentrations of reagents, the instrument is amenable to the determination of fibrinolytic activity in plasma (whether spontaneous or pharmacologically induced) and for the determination of the biologic activity of agents such as urokinase and streptokinase.

The lysis instrument of the present invention may comprise a sample module and an electronic timing module. The timing module indicates which samples are undergoing lysis and records and stores the time required for the process to reach completion. The sample module comprises a heating block assembly with suitable temperature control means which maintains the heating block units at 37° C. The heating block units have wells for receiving test tubes, each adapted to contain a clot and test reagents, with an opaque plastic sphere on top. Insertion of each test tube in its well activates a microswitch, enabling a corresponding latch circuit, permitting a clock pulse to reach an associated counter, and simultaneously activating a flashing green LED indicator, which flashes for each pulse. As lysis progresses, the plastic sphere falls to the bottom, interrupting a light beam. This disables the latch output, stopping the pulse counting and the flashing of the LED indicator. The time count is stored and can be individually displayed for each channel by operating a selector switch. A reset switch is provided for zeroing the instrument.

Accordingly, a main object of the invention is to provide for improved measurement of clot lysis.

Another object is to provide a novel and improved lysis instrument which overcomes the disadvantages and deficiencies of prior art apparatus employed for lysis measurements.

A further object of the invention is to provide an improved lysis instrument employing the principle of measuring the time required for a weight element to drop to the bottom of a container of a dissolving clot under suitable temperature conditions and in the presence of suitable reagents, and including means to improve the accuracy of the time measurement.

A still further object of the invention is to provide an improved lysis instrument of the type employing a ball on top of a clot in a test tube, said clot being subjected to conditions and reagents causing dissolution, whereby the ball drops to the bottom of the test tube, the instrument being automated so as to initiate a time count when the test tube is inserted in the instrument to start dissolution of the clot, and to automatically end said time count when the ball drops to the bottom of the test tube.

A still further object of the invention is to provide an improved lysis instrument of the type employing a temperature-controlled heating block adapted to receive a precooled test tube containing a clot with a reagent such as urokinase or streptokinase to dissolve the clot responsive to heating, and having a ball on top of the clot which drops to the bottom of the test tube responsive to the dissolution of the clot, the time required for the ball to drop after the test tube is inserted in the block being accurately measured automatically and being read out digitally, thereby enabling determination of the biologic activity of said reagent.

A still further object of the invention is to provide an improved lysis instrument of the type employing temperature-controlled block means adapted to receive a plurality of precooled test tubes containing clots with various reagents to dissolve the clots responsive to heating, each havine a ball on its clot which drops to the bottom of its associated test tube responsive to dissolution of the clot, the time required for each respective ball to drop after insertion of its associated test tube in the block means being accurately measured automatically and with high precision, and with means to selectively read out the measured times, whereby to enable determination of the biological activity of the various reagents.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
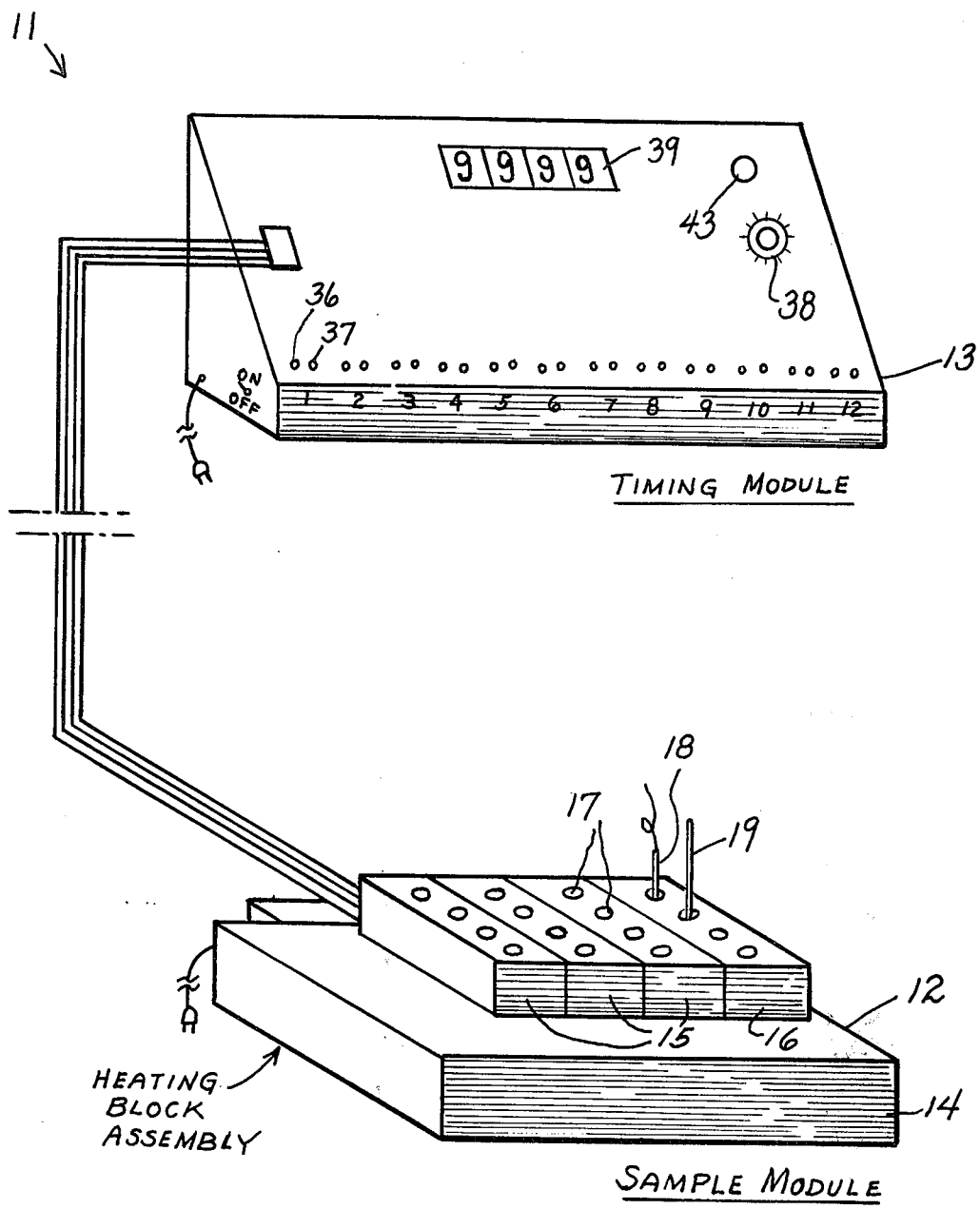
FIG. 1 is a perspective view of the electronic module and of the sample module forming a typical lysis instrument constructed in accordance with the present invention.

Referring to the drawings, FIG. 1 illustrates a typical lysis instrument according to the present invention, designated generally at 11. The instrument 11 comprises a sample module 12 and an electronic timing module 13.

The timing module 13 indicates which samples are undergoing lysis and records and stores the time required for the process to reach completion.

The sample module 12 consists of a heating block 14 provided with conventional electrical heating means, not shown, preferably including solid state temperature control means to minimize RF interference and being designed to maintain the block 14 at 37° C. Mounted on heating block 14 are a plurality of heat-transferring blocks. In a typical embodiment as illustrated in FIG. 1, there are four side-by-side rectangular solid aluminum blocks, each drilled with four vertical wells 17. The blocks comprise three test tube-supporting blocks 15 and an end block 16 for supporting a thermistor-type temperature sensor 18 for controlling the electrical heating means, and a thermometer 19 for providing a visual temperature indication.

Figure 2:
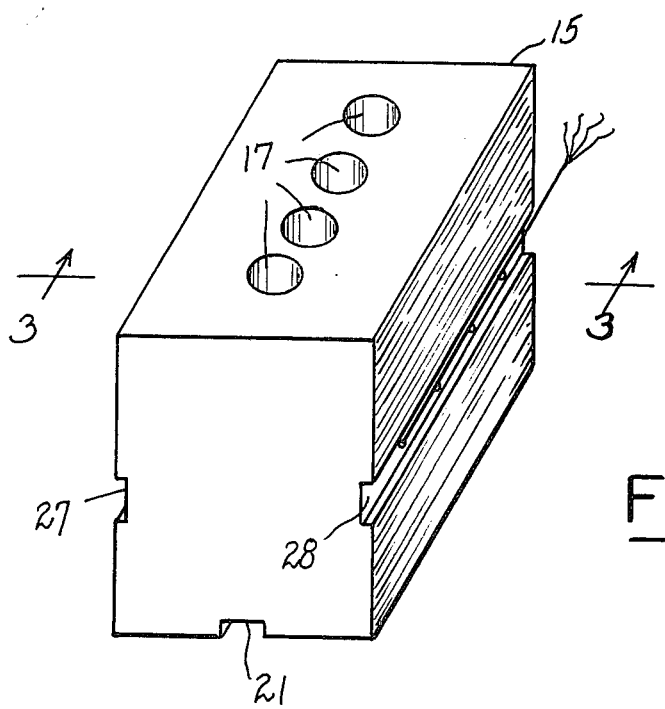
FIG. 2 is a perspective view of one of the test tube-receiving heat-transmitting blocks employed in the sample module of FIG. 1.
Figure 3:
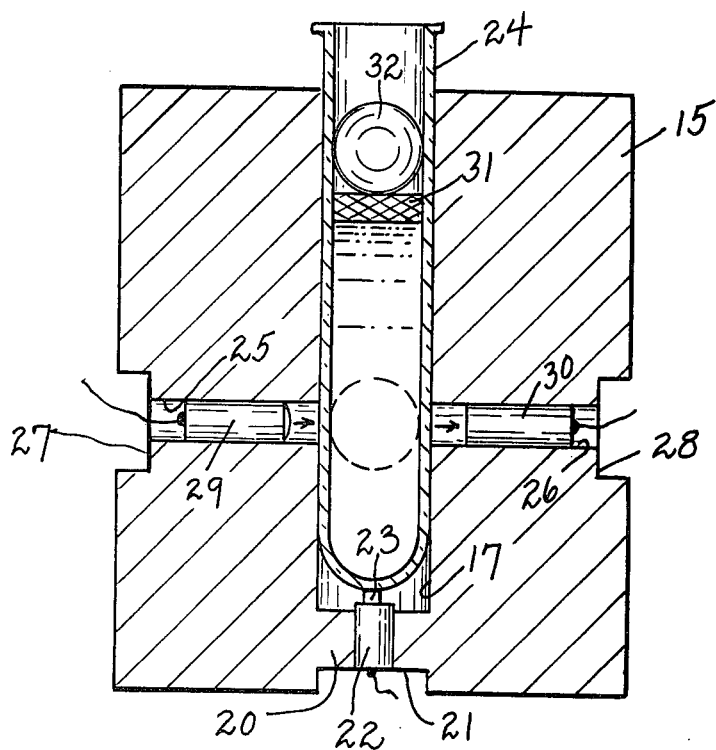
FIG. 3 is an enlarged transverse vertical cross-sectional view taken on the line 3—3 of FIG. 2, shown with a test tube inserted therein, the test tube containing a ball on a clot and associated liquid contents.

As shown in FIGS. 2 and 3, each of the blocks 15 has four vertical test tube-supporting wells 17, each having a bottom wall 20 located above a bottom longitudinal groove 21. Mounted centrally in each bottom wall 20 is a vertical, plunger-type microswitch 22 having a top operating plunger 23. Each vertical well 17 is dimensioned to slidably receive and support a standard test tube 24 in the manner illustrated in FIG. 3.

Transversely aligned horizontal bores 25, 26 are provided in the blocks 15, intersecting the vertical wells 17 and communicating with respective side longitudinal grooves 27, 28 formed in the blocks. As shown in FIG. 3, the transversely aligned bores 25, 26 are arranged to intersect the lower portions of the vertical wells 17 but are spaced above the bottom walls 20 of the wells.

Mounted in each bore 25 is a suitable light source, such as an infra red lamp 29, and similarly mounted in each bore 26 is a suitable photo-sensitive electrical detector, such as a photo-transistor 30. Normally, the beam from lamp 29 impinges on photo-transistor 30 and forms an optical sensor path which controls a circuit associated with the photo-transistor 30 to maintain it closed unless the beam is interrupted.

As shown in FIG. 3, a test tube 24 containing a clot 31 may be inserted in the well 17, with an opaque plastic ball 32 placed on the clot. When the clot dissolves, the ball 32 will descend by gravity and reach a position, shown in dotted view, wherein said optical sensor path is interrupted, which causes the external control circuit associated with photo-transistor 30 to open.

From FIG. 3 it will also be seen that the insertion of a test tube 24 in its associated well 17 causes the associated microswitch plunger 23 to be depressed, which initiates operation of its associated timing circuit, as will be presently described.

The grooves 21, 27 and 28 form guide channels for the lead wires associated with the respective electrical components 22, 29 and 30.

Figure 4:
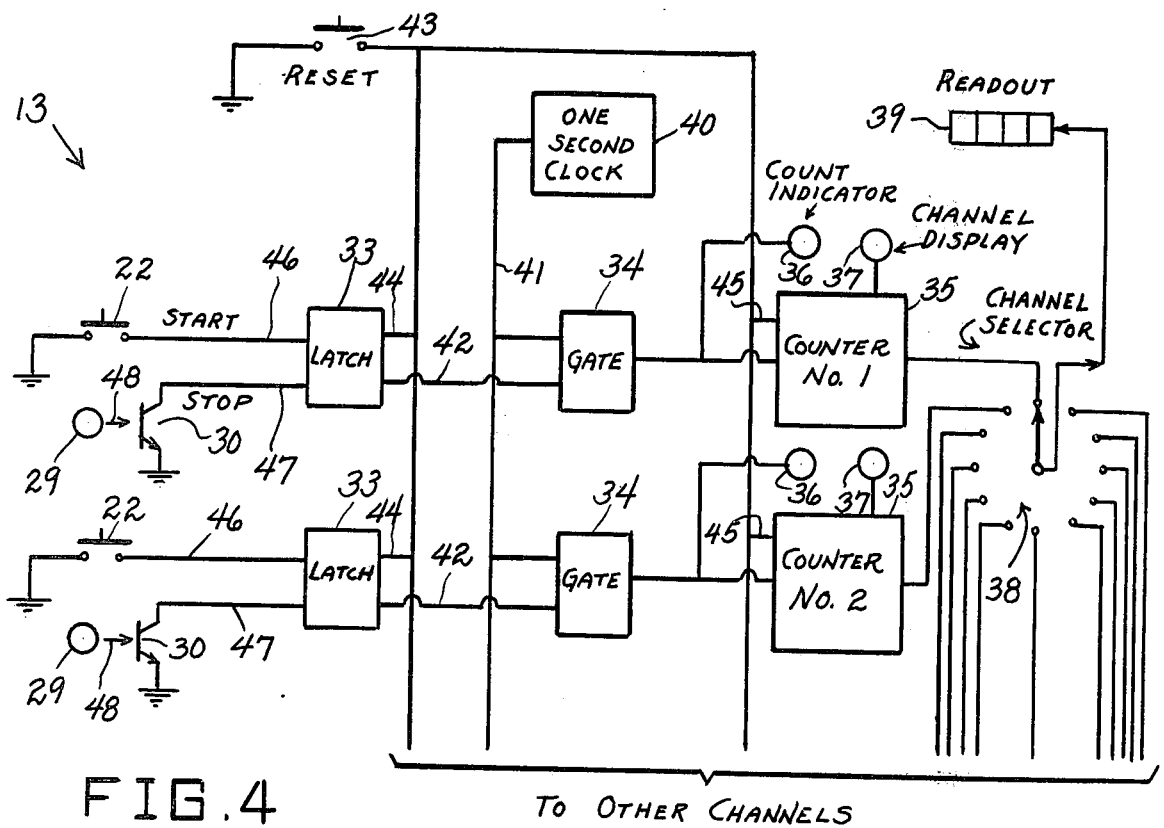
FIG. 4 is a block diagram illustrating the circuitry of the electronic module of FIG. 1.

Referring to FIG. 4, the electronic module 13 comprises a plurality of respective counting channels, one for each of the test tube receiving wells 17 of the blocks 15. Each channel comprises a starting microswitch 22, a conventional integrated circuit latch unit 33, a conventional gate unit 34, and a conventional counter and storage unit 35 having a counter indicator 36 and a steady channel display indicator 37. Unit 36 may comprise a flashing green LED which flashes for every count pulse furnished to its associated counter 35. Unit 37 may comprise a red lamp which provides a steady indication of counter activation, indicating that the associated timing channel is in operation. A rotary selector switch 38 is provided to selectively connect the stored counts of units 35 to a conventional digital readout unit 39.

A conventional one-second pulsing clock unit 40 furnishes clock pulses via a common supply line 41 to one input of each gate unit 34. The latch unit outputs are connected via respective lines 42 to the other inputs of the gate units 34. A common reset switch 43 is provided to simultaneously reset the latch units 33 and the counter and storage units 35. As shown in FIG. 4, the circuitry is arranged so that the reset action takes place responsive to the connection of the reset terminals 44 of the latch units 33 and the reset terminals 45 of the counter and storage units 35 to ground. Similarly, latching occurs responsive to the connection of the latch input terminal wires 46 to ground. Disabling of the latch outputs occurs when the ground connections of the other latch input wires 47 are opened responsive to the interruption of the optical beams, shown at 48.

With its photo-transistor 30 illuminated by its associated infra red lamp 29, a counting channel becomes activated when its microswitch 22 is closed responsive to the insertion of a test tube 24 into its heating well. Closure of the switch 22 enables the associated latch 33, enabling the associated gate 34 via the associated latch output wire 42, and initiating the counting and storing action of the associated counter unit 35.

In a typical procedure, the test cycle is initiated by inserting in the respective heating wells 17 precooled test tubes 24, each containing 1.5 to 2.5 ml of the clot and test reagents, with a plastic opaque sphere 32 on top. For each test tube this activates a microswitch 22, enabling its corresponding latch circuit 33, permitting clock pulses from clock 40 to reach its associated counter 35, and simultaneously activating the associated flashing green indicator LED 36, which flashes for every count pulse. As lysis progresses, the plastic sphere 32 falls to the bottom of its associated test tube 24, interrupting the light beam 48 thereof. This disables the latch output, stopping the pulse counting and the flashing of the LED count indicator 36. The time count is stored in the associated counter unit 35 and can be individually displayed at 39 for each channel by rotating the pole of the selector switch 38. The instrument can be zeroed by operating the reset switch 43.

The apparatus 11 may be employed for the determination of fibrinolytic activity in plasma and for the determination of the biologic activity of lytic agents such as urokinase and streptokinase. In a typical experiment in connection with urokinase, each tube 24 contained the following:

| | |
|---|---|
| Human plasma | 1 ml |
| Urokinase | 1 ml |
| Thrombin | 0.5 ml |
| Final volume | 2.5 ml |

For the purpose of deriving a standard or calibration curve, in three respective test tubes 24 the urokinase was diluted to known concentrations of 200, 100 and 50 units/ml.

Figure 5:
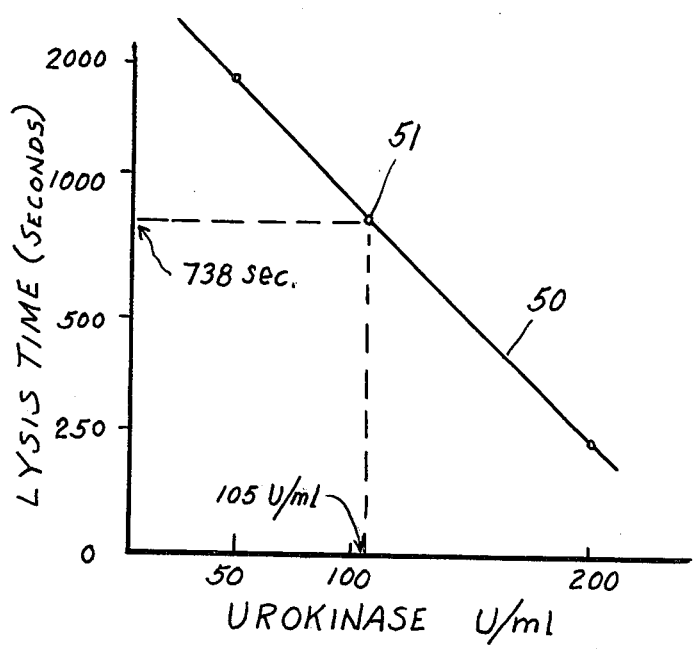
FIG. 5 is a graph representing a calibration curve for determining the concentration of urokinase reagent from the clot-dissolution time obtained from a test employing the lysis instrument of FIGS. 1 to 4.

Immediately subsequent to the addition of the thrombin to each tube, the contents were mixed by inverting twice. The tubes remained in an ice bath until all of the group was mixed. The mixtures formed clots 31. The precooled tubes 24 and contents were placed in their wells 17, with plastic spheres 32 thereon, as above described, and the lysis times for the respective known urokinase concentrations was read out, enabling a calibration curve 50, such as that shown in FIG. 5 to be plotted. Simultaneously with the determination of the data for the calibration curve 50 is was possible to determine the urokinase concentration (U/ml) of an unknown lysed clot in another test tube 24 from the lysing time thereof read out from the instrument 11, said last-named test tube being heated in a well 17 along with the first-named three test tubes, with a plastic sphere thereon. The unknown concentration was found by locating a point 51 on the calibration curve 50, corresponding to the readout time for the unknown. This readout time was about 738 seconds, corresponding on curve 50 to a urokinase concentration of 105 U/ml.

Other lytic agents, such as streptokinase, may be analyzed, using suitable reagents, in a fashion generally similar to the above-described procedure. The instrument 11 may therefore be advantageously employed to measure and automatically record the lysis times of various mixtures. The use of the instrument substantially reduces the laboratory technical workload, especially if a large number of samples must be processed, and if the lysis times to be recorded are very long (as in the case of clinical plasma samples).

An additional advantage of the above-described multi-channel instrument is that it allows for the simultaneous determination of a three point-in duplicate-standard curve and at the same time the assay of an unknown, at multiple concentrations.

The instrument is useful for studies on the standardization of assay systems for the automated determination of high and low molecular weight urokinase, streptokinase, plasminogen, plasmin, fibrinolytic inhibitors, and of clinical plasma samples demonstrating accelerated fibrinolytic activity.

Flexibility in range of timing can be provided by employing different-weight spheres 32. Thus, the gravitational force exerted on the clot 31 can be controlled by using such different-weight spheres.

While a specific embodiment of an improved clot lysing timing instrument has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A clot lysing timing apparatus comprising a heating block assembly formed with a heat transfer well having a closed bottom and adapted to receive and support in a stationary upright position at least one test tube containing a clot and a lysing agent, an opaque weight member adapted to be placed on the clot and to descend therethrough to the lower part of the test tube when the clot dissolves, an electric timer, a start control switch operatively connected to said timer, means mounting said switch in a position in said well to be actuated by a test tube inserted in said well and start said timer, photosensitive enabling means coupled to said timer and located in said heating block assembly at one side of said well, and a light source in said heating block assembly at the opposite side of said well and providing a beam traversing said well and normally illuminating said photo-sensitive means so as to enable said timer, operation of said timer commencing in response to actuation of said switch by a test tube and terminating when said opaque weight member descends in the test tube sufficiently to interrupt said beam.

2. The clot lysing timing apparatus of claim 1, and wherein said timer includes a digital readout means.

3. The clot lysing timing apparatus of claim 1, and wherein said timer includes a flashing count indicator.

4. The clot lysing timing apparatus of claim 1, and wherein said heating block assembly is formed with a plurality of upright heat transfer test tube receiving and supporting wells and said timer comprises respective timer channels, each provided with a control switch operatively connected thereto and located in a position to be actuated by a test tube inserted in a respective well, each well being provided with such photo-sensitive enabling means connected to the respective timer channels and respective light sources normally illuminating the photo-sensitive enabling means across the wells and forming beams which can be interrupted by the descent of weight members placed on clots lysed in the test tubes, common readout means, and means to selectively connect the outputs of the timer channels to said common readout means.

5. The clot lysing timing apparatus of claim 4, and wherein said common readout means is of the digital type and said selective connecting means comprises rotary-pole, multiple-position switch means connected between said readout means and the outputs of the respective timer channels.

6. The clot lysing timing apparatus of claim 1, and wherein said photo-sensitive enabling means comprises a photo-transistor and said light source comprises an infra red lamp.

7. The clot lysing timing apparatus of claim 1, and wherein said timer comprises a clock pulser, an electronic counter, a gate connected between said clock pulser and said counter, latch means operatively connected to said gate, circuit means connecting said photo-sensitive means to said latch means so as to enable the latch means while said beam remains uninterrupted, and circuit means operatively connecting said control switch to said latch means.

8. The clot lysing timing apparatus of claim 7, and a flashing count indicator connected to the output of said gate.

9. The clot lysing timing apparatus of claim 7, and digital readout means connected to the output of said electronic counter.

10. The clot lysing timing apparatus of claim 7, and circuit means to simultaneously reset said counter and said latch means.

11. A clot lysing timing apparatus according to claim 1, wherein said start control switch is a microswitch.

12. A clot lysing timing apparatus according to claim 1, wherein said opaque weight member is a sphere.

13. A clot lysing member according to claim 1, or claim 12 when at least the exterior of said weight member is made of plastic material.

14. A clot lysing member according to claim 1 or claim 12 wherein said weight member is made of plastic material.

* * * * *